United States Patent [19]
Catalano

[11] Patent Number: 4,800,880
[45] Date of Patent: Jan. 31, 1989

[54] SURGICAL NEEDLE HOLDER

[76] Inventor: J. Denis Catalano, 609 Claymont Estates Dr., Ballwin, Mo. 63011

[21] Appl. No.: 912,647

[22] Filed: Sep. 29, 1986

Related U.S. Application Data

[63] Continuation of Ser. No. 654,880, Sep. 26, 1984, abandoned.

[51] Int. Cl.⁴ ............................................. A61B 17/06
[52] U.S. Cl. ..................................... 128/340; D 8/57; 128/321
[58] Field of Search .................. 128/340, 321–346, 128/320, 225, 322, 318; 29/248; 81/426.5; 294/3; D 8/57; 30/212, 261, 262, 268

[56] References Cited

U.S. PATENT DOCUMENTS

| 231,034 | 3/1974 | Moore | D 8/57 |
| 907,064 | 12/1908 | Litzelman | 30/262 |
| 1,069,106 | 8/1912 | Brice | 81/426.5 |
| 1,400,653 | 12/1921 | Barbour | 128/323 |
| 1,533,726 | 4/1925 | Davis | 294/3 |
| 2,962,024 | 11/1960 | Raymond | 128/323 |
| 3,921,478 | 11/1975 | Ygfors | 30/261 |
| 3,921,640 | 11/1975 | Freeborn | 30/261 |
| 4,165,745 | 8/1979 | Heifetz | 128/321 |

FOREIGN PATENT DOCUMENTS

| 81549 | 4/1919 | Austria | 128/322 |
| 666802 | 2/1952 | United Kingdom | 30/262 |

OTHER PUBLICATIONS

United Cutlery & Hardware Products Co., "United & Novelty Review." Feb. 1965, page 75.

Primary Examiner—Richard C. Pinkham
Assistant Examiner—T. Brown
Attorney, Agent, or Firm—Haverstock, Garrett & Roberts

[57] ABSTRACT

A surgical needle holder having a pair of clamping jaws at an obtuse angle to respective elongated handle portions forming a vertex therebetween which are clearly defined. Cooperating latching mechanisms having portions on each handle portion and engageable to hold the handle portions and the respective jaws together to clamp a suturing needle. The jaws are parallel and substantially straight and of uniform cross-section. The handle has two manually grippable portions that cooperate to define a cylinder when the jaws are clamped together. The overall size, shape and weight of the subject needle holder are similar to and feel like a mechanical pencil when held by a surgeon. The needle holder is part of a family of tools having common handle characteristics.

9 Claims, 3 Drawing Sheets

SURGICAL NEEDLE HOLDER

This is a continuation of application Ser. No. 654,880 filed on Sept. 26, 1984 (Abandoned).

BACKGROUND OF THE INVENTION

This invention relates to a surgical needle holder and particularly to a needle holder to be used in delicate surgery. The surgical needle holder of this invention is particularly useful in ocular surgery.

Ocular surgery is more delicate than most of the general surgical operations because of the relatively small size of the parts of an eye and those associated with an eye. The instruments used in ocular surgery usually must have correspondingly delicate or fine operating ends or tips. Also, the ocular surgeon is required to handle and manipulate these instruments in relatively small and sometimes minute increments and degrees. The configuration of the surgical instruments can significantly influence the surgeon's ability to execute these delicate manipulations comfortably, confidently, or even successfully.

An example of frequently performed ocular surgery is one to correct strabismus, an imbalance between the muscular control of one eye relative to the other eye. The muscular control of an eye is done by extraocular muscles, or eye muscles of which there are six for each eye. Each muscle has one end attached to the schlera, the firm outer coat that defines the shape of the eye. The other end of the eye muscle is attached to an annular ring located behind and at the apex of the orbit of the eye. The annular ring is attached to the sphenoid bone and is therefore stationary.

The effective length of one or more of these eye muscles may need surgical alteration to correct a strabismus condition. This is accomplished by cutting the eye muscle from the schlera and re-attaching the severed end of the muscle to the schlera at a different location. During this operation carefully performed, delicate suturing is required.

In this suturing procedure, a needle is held or clamped by a needle holder that in turn is held in a surgeon's hand. The surgeon must manipulate the needle holder to push the suturing needle in one direction into the affected area, then he must work the needle laterally, and thereafter push the needle in another, generally opposite, direction out of the affected area. Also, for many reasons, the penetration points of the needle, both to enter and to leave the affected area, and the lateral traverse of the needle between these penetration points, should be accurately controllable by the surgeon.

In the prior art, there are needle holders that clamp a needle between jaws to hold the needle during a suturing operation. A particular problem with the prior art needle holders is that they are awkward to manipulate for the complete suturing operation. Particular problems associated with prior art needle holders are that they require awkward twisting of the surgeon's wrist and/or arm during a suturing operation and the tip of the needle holder is not oriented to the handle to give the surgeon proper visual as well as physical control of the suturing operation.

The typical prior art needle holder has an elongated handle, to be held in the surgeon's hand, with a needle holding tip that is in line with the axis of the body of the needle holder. This typical conventional needle holder may be held in various ways when starting a suture stitch and all of these ways are awkward, requiring severe bending of the surgeon's wrist and/or arm. Also, this conventional needle holder must be held very differently, requiring changes in the surgeon's grip on the needle holder, each time the direction of the needle is to be changed during the suturing process.

Pursuant to the present invention, there is a way that a needle holder should best be held for control of a suturing operation, for comfort to the surgeon, for steadiness of the surgeon's hand, and for accuracy in the exact points of penetration and of the path of traverse of the needle to complete a suture stitch. The needle holder of this invention can be so held.

An important feature of this needle holder is that the orientation of the needle holding tip relative to the body of the holder allows a manipulating motion of the surgeon's hand to be more natural and comfortable than is possible with needle holders of the prior art. In particular, this needle holder can be held, manipulated and controlled with a few of the smaller, more dextrous muscles of the fingers and hand rather than requiring use of a large number of mucles, including wrist, arm and even shoulder muscles that make delicate control complex and difficult. More particularly, in the present invention, the needle holding tip of the instrument consists of a pair of straight, uniformly fine jaws that are oriented at an obtuse angle relative to the axis of the body of the instrument, and the body has a cylindrical gripping section permitting ready rotation, allowing the needle holder to be held and manipulated in a manner similar to that in which a pencil is held and manipulated. This is particulary important in ocular surgery during which the surgeon frequently needs to simultaneously rotate the needle while pushing it through the tissue. The combination of the cylindrical gripping section on the body with the particular angle between the tip and the axis of the body allows these motions with only a few of the surgeon's hand muscles being involved.

It is particularly important to note that the jaws which form the tip are straight and that the juncture of the jaws to the body of the needle holder is relatively sharp and clearly defined. In the prior art, there are needle holders having a curved tip. Such a configuration makes it difficult for the surgeon to determine the best location on the tip for gripping the needle and produces inconsistency in the angle between the needle and the axis of the handle of the needle holder. Also, as the surgeon proceeds through the suturing operation, it is difficult for him to visualize the precise orientation of the suture needle. In addition, this prior art configuration does not provide a sharp definition between the delicate, fine tip and the relatively more massive body of the needle holder.

The needle holder of the present invention alleviates or eliminates these problems. The jaws of the tip are straight and uniformly fine, with constant small cross-section. An angle is formed between the tip and the axis of the handle to provide maximum control with use of the fewest number of the surgeon's muscles. Since the tip is straight, its entire length defines a single, optimum angle with the axis of the handle. Therefore, the angle of the needle is not altered by where along the tip it is gripped. Furthermore, by observing the angle of the tip relative to the surface being sutured, the surgeon can determine and know the orientation of the needle.

During the course of an operation, a surgeon may need to use a series of different surgical instruments, such as a needle holder, a forceps, a muscle clamp, a muscle hook and others. A problem with the prior art surgical instruments is that different instruments have different weights and different shapes and sizes of handles. Therefore, as he is performing an operation, the surgeon must adapt to the new feel of each instrument as it is handed to him because it will feel strange compared to the instrument the surgeon just used. This lack of consistency in the heft and feel of the surgical instruments can contribute to delay, affect the concentration and perhaps confidence of the surgeon, affect the steadiness with which the surgeon operates, and otherwise interrupt the smooth pace of the operation.

A feature of the present invention is that it provides for a family of ocular surgical instruments wherein the instruments may be different for different surgical purposes, but the weights of the instruments and the size and shape of the handle portions are essentially identical to one another. Thus, when the surgeon moves from one step to another step in the operation, necessitating changes in surgical instruments, the change from one instrument to another does not present an entirely different feeling to the hand of the surgeon but, by contrast, the weight and feel of all of the instruments are consistent to the surgeon.

Another problem with the prior art surgical instruments is that the configuration of the handle is irregular. This irregularity frequently dictates that the instrument can be held in only one or two ways and in only one or two orientations. A feature of the present invention is that the portion of the handle that is held within the fingers of the surgeon is substantially cylindrical, thereby enabling the instrument to be rotated and manipulated infinitesimal amounts as the surgeon may need to do in the course of an operation. The cylindrical shape of the handle greatly reduces the awkwardness of holding and manipulating the surgical instrument during the operaton and keeps the feel of the instrument constant to the surgeon. More particularly, the shape and size of the handle are similar to, and feel like, a mechanical pencil or other writing instrument, causing manipulation of the surgical instrument to resemble that of such a writing instrument. In a family of surgical instruments wherein all have this common cylindrical shaped handle, all the instruments are more accurately controllable and they all feel consistent and familiar to the surgeon.

An object of this invention is to provide a surgical needle holder that can be controlled by relatively few of the small muscles of a surgeon's hand to push, and sometimes simultaneously push and rotate, a needle through flesh being sutured. A related object is to provide such a surgical needle holder wherein the surgeon can observe the orientation of the tip of the needle holder to determine precisely the orientation of the suture needle and can respond to such observation with necessary and desired accurate minute manipulations of the surgical needle holder.

Another object of the invention is to provide a surgical needle holder that is particularly adapted to the requirements of very delicate ocular surgery and that has a tip consisting of a pair of fine jaws that are straight and joined at a distinctly defined obtuse angle to a more massive handle.

A further object of the invention is to provide a surgical needle holder that has a handle with a cylindrical gripping section adapted to be held between the thumb and fingers of a surgeon's hand wherein the handle is long enough to have an end section resting against the hypothenar space of the hand, the other end of the needle holder having a tip for clamping a suture needle, such that the needle holder feels similar to and can be manipulated like a mechanical pencil.

Still another object of the invention is to provide a surgical needle holder which is one of a family of surgical instruments all of which have in common a handle section of cylindrical shape, the lengths and diameters of the handle sections being similar and the overall weights of the instruments being similar, thereby presenting a consistent and familiar heft and feel to the surgeon as he is handed various ones of the instruments in sequence during the course of a surgical operation.

Other objects and advantages will be apparent from the description and claims of the invention.

SUMMARY OF THE INVENTION

The surgical needle holder of this invention has an elongated body with a needle clamping tip projecting from one end thereof. In the preferred construction, the body consists of two complementary elements and the tip consists of two complementary jaws, each associated with a respective one of the body elements. Pre-sprung leaf springs bias the body elements and jaws toward a separated or open position. The body elements have semi-cylindrical handle sections adapted to be held between the thumb and fingers of a surgeon's hand. When these handle sections are squeezed together to a closed position overcoming the force of the leaf springs, the jaws are brought together into needle clamping position.

Each jaw and the axis of its associated body element intersects at an obtuse angle, the vertex of which is distinctly defined. The jaws are delicate and of substantially uniform small cross-section compared to the relatively more massive body whose shank begins at the aforesaid vertex.

A latching mechanism releasably locks the body elements in the closed position. In this position, the two semi-cylindrical handle sections cooperate to define susbtantially a cylinder. The surfaces of these handle sections are preferably knurled.

The size of the body, shape of the handle (defined by the two handle sections in the closed position) and overall weight of this surgical needle holder are similar to those physical characteristics of other surgical instruments, thus defining a family of surgical instruments that are comfortable and familiar in heft and feel when handled in sequence by a surgeon.

DESCRIPTION OF THE PREFERRED EMBODIMENT OF THE INVENTION

Figure 2:
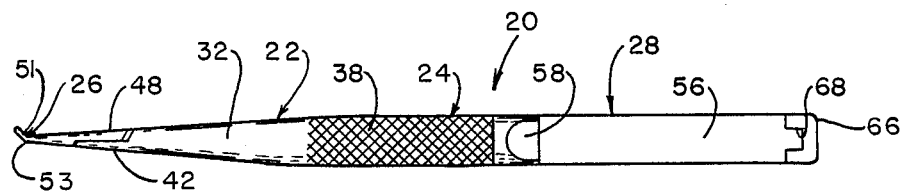
FIG. 2 is a right side elevational view of the surgical needle holder.

Referring to the drawings more particularly by reference numbers, this surgical needle holder 20, preferably made of stainless steel, has an elongated body 22 consisting of a handle section 24, a tip 26, and a spring section 28. A latching mechanism 30 holds the needle holder in clamping condition or releases it to open condition, as will be described.

The body 22 has two complementary body elements 32 and 34 held together by and pivotal about a set screw 36. The body element 32 has a knurled gripping section 38 that is shaped like half a cylinder and forms half the handle section 24. Forward of the gripping section 38, the body element 32 has a tapered elongated shank 40 that leads to a forward end 42.

Likewise, the other body element 34 has a knurled gripping section 44 that is also shaped like half a cylinder and forms the other half of the handle section 24. Forward of the gripping section 44 there is a tapered elongated shank 46 leading to a forward end 48. The forward ends 42 and 48 of the body elements 32 and 34 are where the set screw 36 penetrates to hold the body elements together.

A jaw 50 extends from the forward end 42 of the body element 32. A complementary jaw 51 extends from the forward end 48 of the body element 34. The jaws 50 and 51 together constitute the tip 26 where a surgical needle is held during a suturing operation. These jaws 50 and 51 are preferably formed as integral parts of the body elements 32 and 34. The relationship of the jaws 50 and 51 to the body elements 32 and 34 is a particularly important feature of the invention. The jaws 50 and 51 extend from the body elements 32 and 34 at an obtuse angle preferably within the range of 135°-140°. This angle and its significance will be more fully discussed hereinafter. The vertex or apex 52 on the lower side of the intersection between the jaw 50 and the shank end 42 and the vertex or apex 53 on the lower side of the intersection of the jaw 51 and the shank end 48 are relatively sharply defined. The jaws 50 and 51 are preferably relatively straight, as shown in the drawings, and have flat inner faces 54 and 55, respectively (FIG. 10) along the entire length of the tip 26. The jaws are of substantially uniform cross-section, each being approximately 0.4 mm wide (tranverse to the face 54 or 55), 0.5 mm high (parallel to that face), and 2 mm long to the apex (52 or 53). In contrast, the body elements are relatively more massive, beginning immediately at their forward ends 42 and 48 adjacent the apex 52 and 53.

Figure 4:
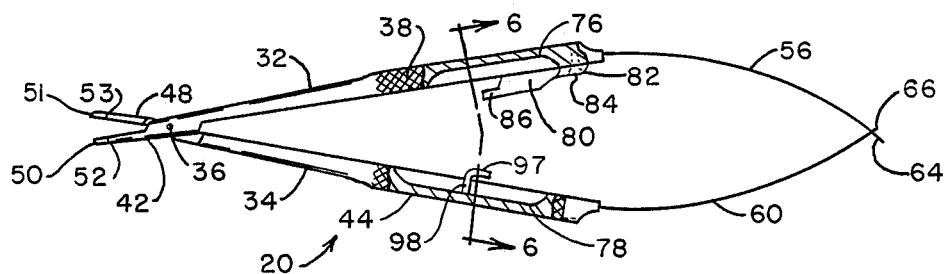
FIG. 4 is a bottom plan view of the surgical needle holder and with the needle holder in the open position.
Figure 5:
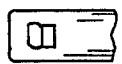
FIG. 5 is a partial left side elevational view of the rear portion of the surgical needle holder.

The spring section 28 includes a leaf spring 56 that is welded to the back end 58 of the knurled gripping section 38. The leaf spring 56 is pre-sprung to seek the bowed unstressed shape, when released, that is shown in FIG. 4. A complementary leaf spring 60 that is the other half of the spring section 28 is welded to the back end 62 of the knurled gripping section 44. The leaf spring 60 is pre-sprung to seek the bowed unstressed shape shown in FIG. 4. The free or rear ends 64 and 66, respectively, of the leaf springs 56 and 60 are connected together by a slot 68 and a tab 70 (FIG. 5). This tab 70 has lateral ears 72 that keep the tab 70 from slipping from the slot 68. The connection resulting from the slot 68 and the tab 70 keeps the free ends 64 and 66 of the leaf springs 56 and 60 connected together while allowing them to swing or pivot at the connection. The pre-sprung nature of the leaf springs 56 and 60 is such that if allowed to do so, they will spring to the positions and shapes illustrated in FIG. 4. Because the springs 56 and 60 are rigidly welded to the ends 58 and 62 of the handle elements 38 and 44, when the springs are released, they cause the body elements 32 and 34 to pivot about the set screw 36 and spread to the position as shown in FIG. 4. This spreads the jaws 50 and 51. To move the body elements 32 and 34 together and pivot the jaws 50 and 51 together as shown in FIG. 1, an external force must be applied to overcome the opposing resistance of the leaf springs 56 and 60.

Figure 1:
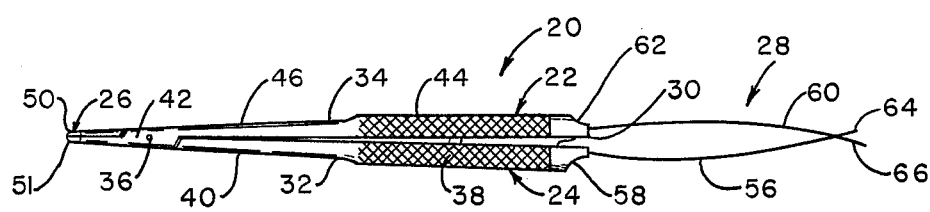
FIG. 1 is a top plan view of the surgical needle holder showing the holder in a closed position.

Since the springs 56 and 60 tend to hold the body elements 32 and 34 separated, the latching mechanism 30 is provided to releasably hold the body elements 32 and 34 together in the relative positions generally illustrated in FIG. 1. In the preferred embodiment, the latching mechanism 30 is releasable by another manual force so that the body elements can be sprung by the leaf springs to the open position shown in FIG. 4.

Figure 7:
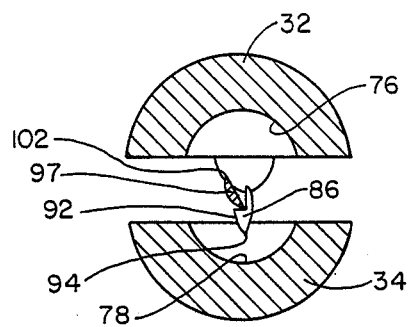
FIG. 7 is an enlarged view in section of the surgical needle holder similar to that of FIG. 6, but with the needle holder in clamping condition.
Figure 8:
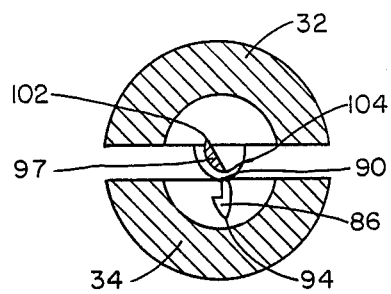
FIG. 8 is an enlarged view in section of the surgical needle holder similar to that of FIG. 6 but showing the latching mechanism in the released condition obtained upon squeezing the two handle parts together.

The components of the latching mechanism fit within recesses 76 and 78 on the inner sides of the body elements 32 and 34 (FIG. 7). These recesses 76 and 78 serve a dual purpose. One is the elimination of metal from the body elements 32 and 34 to adjust the overall weight of the needle holder to an optimum weight as well as to a weight that is similar to that of other ocular surgical instruments. The other purpose of the recessed 76 and 78 is that they allow the latching mechanism 30 to fit between the body elements 32 and 34 even when the body elements are in the closed positions shown in FIG. 1 or in the compressed positions shown in FIG. 8.

The latching mechanism 30 includes a blade 80 projecting from a base 82 that is fastened to the body element 32 by a set screw 84 or by other means. The blade 80 is made of a spring-like material such as spring steel so that when forced by a camming action, it will swing or bend laterally relative to the base 82.

The blade 80 has a forwardly projecting lug 86 on which there is a generally horizontal seat 87 with a vertical stop 88 next to it. A cam surface 89 intersects the vertical stop 88 at an upper edge 90. Another cam surface 92 intersects the face of the cam surface 89 at a lower edge 94 and intersects the outer side of the horizontal seat 87 at an upper edge 96.

A keeper 97 projects horizontally from a base 98 that is welded or otherwise secured to the body element 34 at the bottom of the recess cavity 78. The keeper 97 is rigidly mounted, as distinguished from the blade 80. The keeper 97 has an inclined cam surface 100 that extends between an upper edge 102 and a lower edge 104. Another cam surface 106 extends from the upper edge 102 to the lower edge 104. When the lug 86 is free of the keeper 97, as is the case illustrated in FIGS. 6 and 8, for example, the edge 90 is to the left of the edge 104 and the edge 94 is to the right of the edge 102.

The latching mechanism 30 functions as follows. When the body elements 32 and 34 are squeezed together from the positions shown in FIG. 4 toward the positions shown in FIG. 1, the keeper 97 approaches the lug 86. Since the edge 94 of the lug 86 is to the right of the edge 102 of the keeper 97, the edge 102 contacts the cam face 92. With continued squeezing pressure, the lug edge 102 and the cam surface 100 slide along the cam surface 92 of the lug 86, pushing the lug 86 to the right as viewed in FIG. 6 as the blade 80 bends. When the edge 104 of the keeper 97 reaches and passes slightly above the edge 96 of the lug 86, the lug 86, forced by the pre-sprung blade 80, snaps to the left until the vertical stop 88 contacts the edge 104 of the keeper 97.

Now, when the gripping pressure on the body elements 32 and 34 is released, the leaf springs 56 and 60 exert a spreading force on the body elements 32 and 34. However, now the keeper 97 is held against the seat 87 of the lug 86 as shown in FIG. 7 to hold the body elements 32 and 34 in the closed condition illustrated in FIG. 1. In this condition, a needle N (see FIG. 10) will be held tightly clamped between the jaws 50 and 51 of the tip 26.

It is in this latched condition that the needle holder functions during suturing. The needle N is held tightly clamped. The body elements 32 and 34 are closed, and the gripping sections 38 ad 44 cooperate to define essentially a cylinder.

To release the needle N, further gripping pressure is applied to the handle elements 32 and 34, moving them further toward one another. This causes the keeper 97 to slide up the vertical stop 88 of the lug 86 until the edge 104 of the keeper reaches and passes above the edge 90 of the lug 86. This releases the lug to allow the pre-sprung blade 80 to swing the lug further to the left to the position illustrated in FIG. 8, with the edge 104 of the keeper 97 to the right of the edge 90 of the lug 86.

Figure 6:
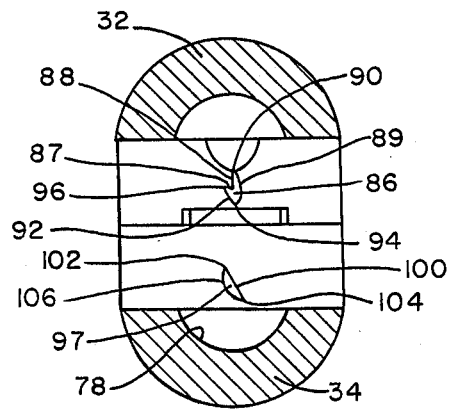
FIG. 6 is an enlarged view in section of the surgical needle holder taken along the line 6—6 of FIG. 4 with the needle holder in open condition.
Figure 3:
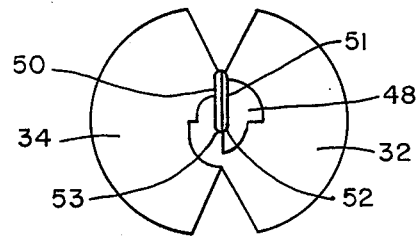
FIG. 3 is an enlarged front end view of the surgical needle holder, as viewed from the left of FIG. 1.

Now, as the gripping pressure is released, the leaf springs 56 and 60 urge the body elements 32 and 34 apart. The cam face 106 of the keeper 97 contacts the cam face 89 of the lug 86. As the keeper 97 moves downwardly relative to the lug 86, as viewed in FIG. 8, the cam face 106 slides along the cam face 89 pressing the lug 86 to the left as viewed in FIG. 8. Finally, when the edge 102 of the keeper 97 reaches and moves below the edge 94 of the lug 86, the lug 86 is released to be swung to its left-most starting location, by the force of pre-sprung blade 80, as illustrated in FIG. 6.

Several physical characteristics of this surgical needle holder 20 are significant. The overall weight of the needle holder 20 is similar to the weight of a typical mechanical pencil, approximating one ounce, or slightly less. The diameter of the cylinder defined by the gripping sections 38 and 44 in the closed condition illustrated in FIGS. 1 and 7 is preferably about ⅜ inch. The length of the gripping sections 38 and 44 is about 1¼ inch. The length of the body including the gripping sections 38 and 44 and the spring section 28 is about 3¼ inches.

Now that the basic structural form of this surgical needle holder has been described, its use and advantages can be set forth. With a needle N, with its trailing suture thread A, clamped between the jaws 50 and 51 and the body elements 32 and 34 latched in the closed condition shown in FIG. 1 and 7, the needle holder 20 can be used for suturing. It should be noted that the needle N is usually held perpendicularly to the jaws 50 and 51 between the flat faces 54 and 55. Since the jaws 50 and 51 of the present needle holder are preferably relatively straight and of uniform cross-section, the desired orientation of the needle can be achieved regardless of where along the tip the needle is gripped. Also, the spans of the faces 54 and 55 in contact with the needle will be unaffected by where the needle is gripped.

Figure 9:
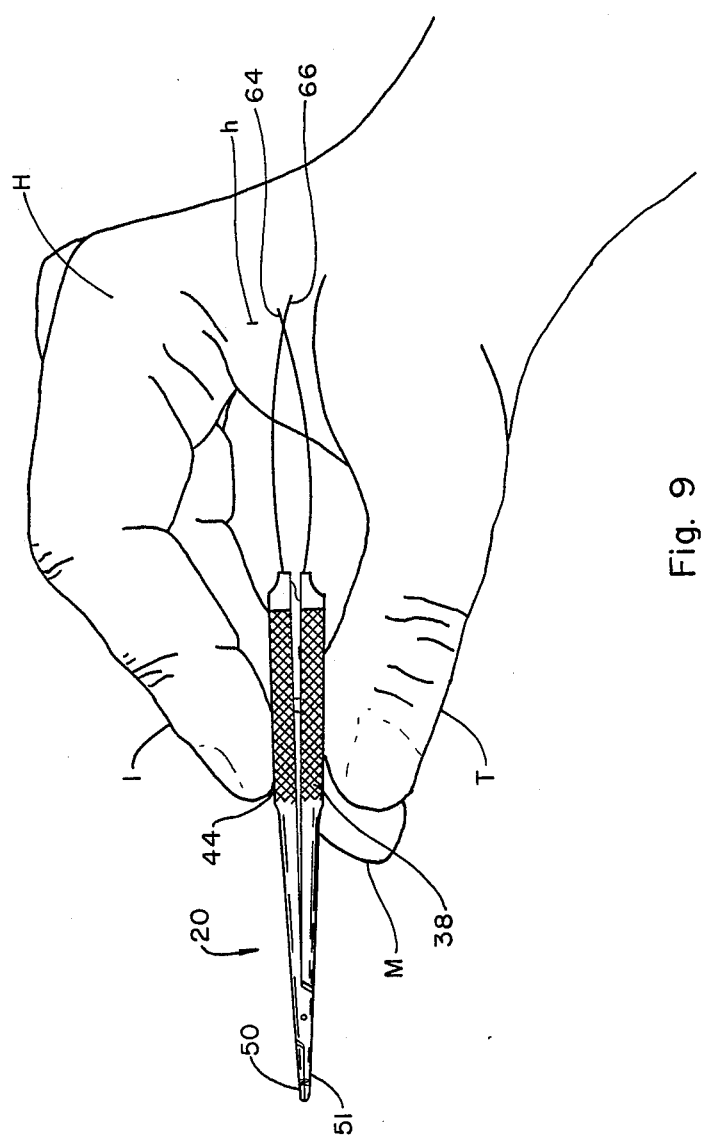
FIG. 9 is a perspective view of the surgical needle holder illustrating how it is held in a surgeon's hand during use.

The needle holder is held in the surgeon's hand H much like a pencil, as illustrated in FIG. 9. Typically, the knurled gripping sections 38 and 44, which now cooperate to define a cylinder, are held by the thumb T, the index finger I and the middle finger F, as shown. The back of the needle holder defined by the ends 64 and 66 rests against the hypothenar space h of the hand H as shown, thereby giving stability to the manipulation and holding of the needle holder 20.

Figure 10:
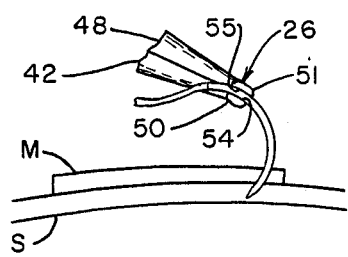
FIG. 10 is a schematic partial view of the surgical needle holder illustrating insertion of a surgical needle into the affected tissue area at the beginning of a suturing stitch.
Figure 11:
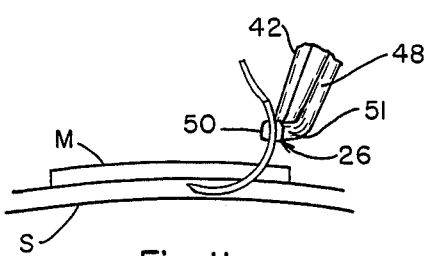
FIG. 11 is a schematic partial view similar to that of FIG. 10, but illustrating the position of the needle holder as the suture needle is pushed through the lower tissue layer.
Figure 12:
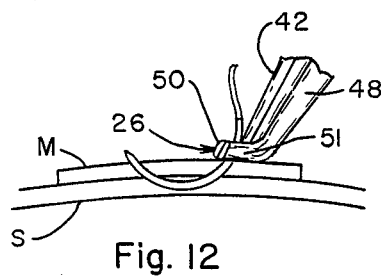
FIG. 12 is a schematic partial view similar to those of FIGS. 10 and 11, but illustrating the orientation during return of the needle from the affected area.

FIGS. 10, 11 and 12 schematically illustrate the positions of the needle holder 20 during an ocular suturing operation. In the example illustrated, an eye muscle M is being sutured to the schlera S of an eyeball. For each of the various positions of the needle holder 20, such as those shown in FIGS. 10, 11 and 12, the needle holder can be held in the general manner that is shown in FIG. 9. The tip 26 can be readily, comfortably and accurately rotated by the small muscles of the thumb T and fingers I and F rotating the cylinder defined by the gripping surfaces 38 and 44. Because of the angulation of the tip 26 to the axis of the body 22, these same thumb and finger muscles, sometimes with a small number of hand and/or forearm muscles, can accomplish the swinging movement needed to move the curved needle N through the affected area in the sequence shown in FIGS. 10, 11 and 12.

In FIG. 10, the needle N has been pushed through and into the affected area. In FIG. 11, the needle holder 20 has been swung by the surgeon about the horizontally held tip 26. It is also usually helpful or necessary to simultaneously rotate the needle holder about the axis of the body 22 to cause the needle N to "plow" through the tissue of the schlera. Thus, there is a combined swinging of the needle holder about the tip 26, rotation of the handle 22, and pushing of the needle further through the tissue of the affected area (the muscle M and schlera S).

FIG. 12 shows the return or completion of the stitch from the affected area. Here, the tip 26 has been pushed all the way to the muscle M. Note that through the entire sequence, the tip 26 has been held generally parallel to the affected area of the muscle M and schlera S. Because the tip 26 is flat, there is minimum interference with the suturing when the tip contacts the muscle M. The needle holder 20 can be easily released from the needle N and thereafter reclamped to the leading end of the needle to continue the procedure and to pull the needle through.

Because of the angle between the tip 26 and the axis of the body 22, the needle holder 20 can be held as generally illustrated in FIG. 9 regardless of the direction of the needle (FIGS. 10, 11 or 12). This angular relationship of the tip permits pivoting manipulation of the needle holder by movement of the thumb T, index finger I, and middle finger F just as is true to rotate the needle holder about the axis of the body 22.

Also, the size, shape and weight of this surgical needle holder are similar to those of a mechanical pencil so holding and using the needle holder are comfortable and familiar to the surgeon. In addition, contemplating the same handle design with the same size and shape and same overall weight among a variety of surgical instruments makes them all comfortable and familar to the surgeon.

It can be seen that each of the features of this surgical needle holder has significant advantages. Also, each of these features contributes to an overall effect of handling ease, comfort, accuracy and consistency of the needle holder.

Thus there has been shown and described a novel surgical instrument especially useful for ocular surgery, which fulfills all of the objects and advantages sought therefor. It will be apparent to those skilled in the art, however, that many changes, modifications, variations and other uses and applications for the subject tool are possible. All such changes, modifications, variations and other uses and applications which do not depart from the spirit and scope of the invention are deemed to be covered by the invention which s limited only by the claims which follow.

What is claimed is:

1. A surgical instrument adapted to grip a suturing needle utilized in connection with optical surgery comprising:
   first and second elongated handle members each having a forward end and rearward end and a substantially semi cylindrical surface and an opposite facing surface, said handle members being hingedly connected adjacent the forward ends thereof, spring means connecting said first and second handle members adjacent the rearward end thereof, said connecting means normally biasing the rearward ends of said handle members away from each other to a first position wherein said handle members are angularly related,
   first and second jaw members each being integral with the forward end of a respective one of said handle members and extending therefrom at an obtuse angle, said first and second jaw members being adapted to cooperate with one another to grip a suturing needle therebetween when said first and second handle members are moved toward each other to a second position wherein said handle members are in more nearly substantially parallel relationship adjacent each other whereby the semi cylindrical surfaces on the respective handle members together form a substantially cylindrical gripping surface, and
   releasable latching means having cooperatively engageable portions on the respective handle members, said latching means including a recess in the facing surface of one of said handle members, at least a portion of the latching means on said one handle member being located in the recess, another portion of the latching means being on the other handle member in position such that when the handle members are in said second position as with a needle clamped between said jaw members in opposition to said biasing means the latching means on the respective handle members are able to become engaged or disengaged with each other by gripping pressure to hold the handle members together and by relative lateral movement of the handle members with respect to each other so that the latching means can become engaged or disengaged.

2. The surgical instrument of claim 1 wherein each of said first and second handle members includes a gripping section having a substantially semi-cylindrical cross-sectional outer surface and a planar surface opposite therefrom, at least one of said gripping sections having said recess formed in the planar surface thereof at an intermediate location therealong, said recess being adapted to receive the latching means associated with the other handle member whereby said handle members can be latched when they are moved substantially together and laterally.

3. The surgical instrument of claim 2 wherein said latching means includes a pair of hook members, one mounted on each of the handle members including one being located in said recess, each of said hook members having a surface thereon angularly oriented at an acute angle relative to the respective plane surfaces of the handle members whereby the surfaces of the hook members engage and slide past one another and in so doing at least one of the hook members is deflected transversely of the other hook member so that a portion of one of the hook members is able to move behind a portion of the other hook member when the handle members are moved to the second position to maintain the second position thereof with a needle clamped in position between the jaw members in opposition to the means biasing the handle members away from each other.

4. The surgical instrument of claim 2 wherein the gripping section of each of said first and second handle members is knurled along the substantially semi-cylindrical shaped surface thereof.

5. The surgical instrument of claim 1 wherein each of said first and second jaw members is an integral elongated element projecting from the forward end of a respective one of said handle members at said obtuse angle, is of substantially smaller cross-sectional area than the respective handle member, is substantially straight from where it meets the respective handle member to the end of said jaw member and said first and second jaw members are substantially parallel in the second position of the handle members.

6. The surgical instrument of claim 1 wherein the obtuse angle of the jaw members relative to the handle members is within the range from about 105° to about 150°.

7. The surgical instrument of claim 1 wherein the obtuse angle of the jaw members relative to the handle members is within the range of from about 130° to about 140°.

8. An instrument for holding a suturing needle used in optical surgery comprising:
   a pair of similar elongated handle members each having a hand gripping portion of substantially semi-circular cross-section and opposed plane surface and at least one having a recess in the plane surface thereof,
   means hingedly connecting the handle members adjacent corresponding forward ends thereof whereby the handle members are able to be moved between an open position in which the handle portions are angularly related to each other and a closed position wherein the handle members are substantially adjacent one another and substantially parallel to each other and the gripping portions thereof define a substantially cylindrical outer hand gripping surface, means connecting the ends of the handle members opposite the hinged connecting means, said connecting means including spring means normally biasing said opposite ends of the handle members toward the open position, a pair of needle engaging jaw members connected respectively to the handle members on the opposite side of the hinged connecting means from the respective handle portions, said jaw members forming obtusely angularly related integral extensions of the respective handle members whereby the jaw members move into needle engaging position when the handle portions are moved to said closed position, and cooperatively engageable latch means having portions on the respective handle portions and laterally movable into cooperative engagement and disengagement when the handle portions are in their closed position, said latch means being at least partially accommodated within the recess in at least one of said handle portions when the handle portions move to the closed position to latch the handle portions in said closed position and maintain the jaw members in clamped engagement.

9. The instrument of claim 8 wherein each handle portion has a semi-cylindrical outer surface and a plane surface opposite therefrom, at least one of said handle portions having the said recess formed in the plane surface therein at an intermediate location therealong, the means on and between the handle portions including a pair of hook members, one mounted on each of the handle portions including one located in the recess, each of said hook members having a surface thereon oriented at an acute angle relative to the respective plane surface of the handle members whereby the surfaces of the hook members engage each other and slide past one another to engage the hook members when the handle portions are moved to their closed position to maintain the closed and clamped position thereof in opposition to the means biasing the handle portions apart.

* * * * *